(12) United States Patent
Bontus et al.

(10) Patent No.: US 8,396,274 B2
(45) Date of Patent: Mar. 12, 2013

(54) IMAGING SYSTEM

(75) Inventors: Claas Bontus, Hamburg (DE); Michael Grass, Buchholz in der Nordheide (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1049 days.

(21) Appl. No.: 12/438,559

(22) PCT Filed: Aug. 28, 2007

(86) PCT No.: PCT/IB2007/053442
§ 371 (c)(1),
(2), (4) Date: Feb. 24, 2009

(87) PCT Pub. No.: WO2008/026153
PCT Pub. Date: Mar. 6, 2008

(65) Prior Publication Data
US 2009/0208077 A1    Aug. 20, 2009

(30) Foreign Application Priority Data

Aug. 31, 2006 (EP) .................................. 06119922

(51) Int. Cl.
*G06K 9/00* (2006.01)
(52) U.S. Cl. ........................................................ 382/131
(58) Field of Classification Search .................. 382/131
See application file for complete search history.

(56) References Cited

U.S. PATENT DOCUMENTS

| | | | |
|---|---|---|---|
| 5,933,517 A * | 8/1999 | Grangeat et al. ............. | 382/131 |
| 6,014,419 A | 1/2000 | Hu | |
| 6,480,561 B1 | 11/2002 | Proksa | |
| 7,929,747 B2 * | 4/2011 | Chen ............................ | 382/131 |
| 2002/0131544 A1 | 9/2002 | Aradate et al. | |
| 2006/0109950 A1 | 5/2006 | Arenson et al. | |
| 2006/0182216 A1 | 8/2006 | Lauritsch et al. | |

FOREIGN PATENT DOCUMENTS

| | | |
|---|---|---|
| WO | 03083778 A1 | 10/2003 |
| WO | 2004044849 A1 | 5/2004 |
| WO | 2005104038 A1 | 11/2005 |

(Continued)

OTHER PUBLICATIONS

Yu et al., Region of Interest Reconstruction From Truncated Data in Circular Cone-Beam CT, IEEE Transactions on Medical Imaging [on-line], Jul. 2006, vol. 25, Issue: 7, pp. 869-881. Retrieved from http://ieeexplore.ieee.org/xpls/abs_all.jsp?arnumber=1644803.*

(Continued)

*Primary Examiner* — Matthew Bella
*Assistant Examiner* — Dennis Rosario

(57) ABSTRACT

The present invention relates to an imaging system for imaging a field of interest, in particular to a computed tomography system. The imaging system comprises an irradiation unit (2) which moves relative to a field of interest along a first trajectory (501) and along a second trajectory (503). While the irradiation unit (2) moves along the first trajectory (501), first detection data are acquired and, while the irradiation unit (2) moves along the second trajectory (503), second detection data are acquired. An intermediate image of the field of interest is reconstructed from at least the second detection data, and virtual detection data are determined by forward projection through the intermediate image. Finally, an image of the field of interest is reconstructed from the first detection data and the virtual detection data.

20 Claims, 10 Drawing Sheets

FOREIGN PATENT DOCUMENTS

WO 2006038145 A1 4/2006

OTHER PUBLICATIONS

Bontus, C., et al.; A quasiexact reconstruction algorithm for helical CT using a 3-Pi acquisition; 2003; Med. Phys.; 30 (9)2493-2502.

Dennerlein, F., et al.; Exact and efficient cone-beam reconstruction algorithm for a short-scan circle combined with various lines; 2005; Medical Imaging-Image Processing; SPIE; vol. 5747:388-399.

Kachelriess, M., et al.; 4D Reconstruction for Wide Cone-Angle Medical CT; 2003; IEEE Nuclear Science Symposium Conf. Record; vol. 5:3248-3252.

Katsevich, A.; Image reconstruction for the circle and line trajectory; 2004; Phys. Med. Biol.; 48:5059-5072.

Bontus, C., et al.; EnPiT: Filtered Back-Projection Algorithm for Helical CT Using an n-Pi Acquisition; 2005; IEEE Trans. on Medical Imaging; 24(8)977-986.

Stevendaal, U. van, et al.; ECG gated Continuous Circular Cone-Beam Multi-cycle Reconstruction for In-Stent Coronary Artery Imaging: A Phantom Study; 2006; Proc. of SPIE; vol. 6142:61420L1-10.

* cited by examiner

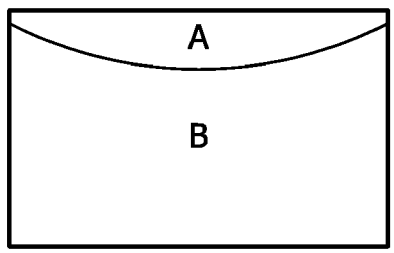
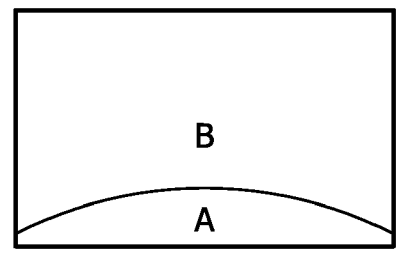
FIG. 20  FIG. 21
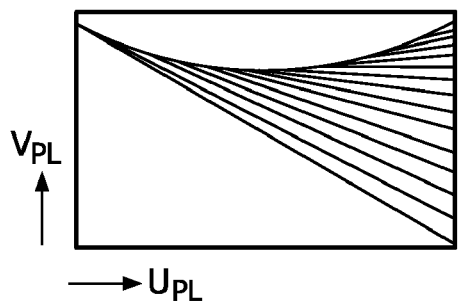
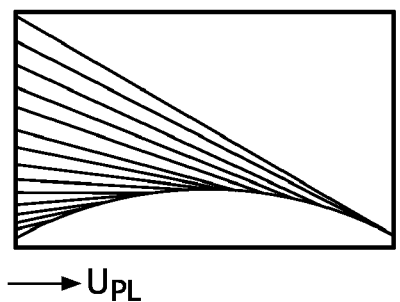
FIG. 22  FIG. 23
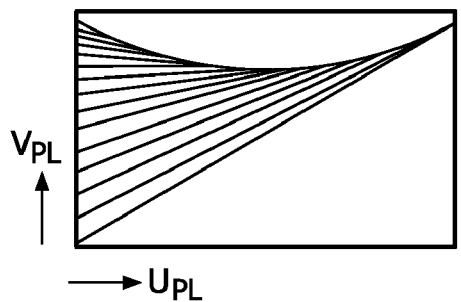
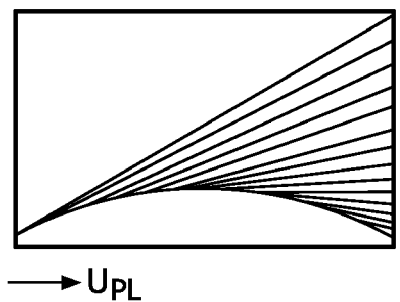
FIG. 24  FIG. 25

IMAGING SYSTEM

FIELD OF THE INVENTION

The present invention relates to an imaging system, an imaging method, and a computer program for imaging a field of interest. The invention further relates to an image generation device, an imaging generation method, and a computer program for generating an imaging of a field of interest.

BACKGROUND OF THE INVENTION

Imaging systems are known, for example computed tomography systems (CT systems) which are adapted to irradiate a field of interest with radiation of an irradiation unit, like an X-ray tube which is moved relative to the field of interest along a first trajectory and along a second trajectory. First detection data and second detection data are acquired by a detection unit in dependence on the radiation after having passed the field of interest while the radiation source travels along the first and the second trajectory, respectively. The first and the second detection data are used to reconstruct an image of the field of interest. Such an imaging system is, for example, disclosed in "Exact and efficient cone-beam reconstruction algorithm for a short-scan circle combined with various lines" by F. Dennerlein et al., Medical Imaging 2005: Image Processing, edited by J. Michael Fitzpatrick, Joseph M. Reinhardt, Proceedings of the SPIE, Vol. 5747 (SPIE, Bellingham, Wash., 2005).

These known imaging systems have the disadvantage that the reconstruction process is limited by the run of the first and second trajectories. For example, if, after acquiring first and second detection data, the reconstruction process needs non-detected data which should have been acquired with the irradiation unit traveling along a certain trajectory, the acquisition has to be repeated in order to detect the missing data, so that the radiation dose applied to the field of interest, for example to a patient, increases. In order to overcome this drawback, the acquisition process, in particular the run of the first and the second trajectories, has to be planned carefully, which complicates the acquisition protocols of know imaging systems.

SUMMARY OF THE INVENTION

It is an object of the present invention to provide an imaging system wherein the reconstruction process is not limited by the run of the first and the second trajectories as described above.

In a first aspect of the present invention, an imaging system for imaging a field of interest is provided, comprising:

an irradiation unit emitting radiation for irradiating the field of interest, a moving unit for moving the irradiation unit relative to the field of interest along a first trajectory and for moving the irradiation unit along a second trajectory, a detection unit for detecting first detection data depending on the radiation after passing through the field of interest, when the irradiation unit is moved along the first trajectory, and for detecting second detection data depending on the radiation after passing through the field of interest, when the field of interest is irradiated along the second trajectory, a reconstruction unit for reconstructing an intermediate image of the field of interest from at least the second detection data and for reconstructing an image of the field of interest from the first detection data and virtual detection data, a forward-projection unit for determining the virtual detection data by forward projection through the intermediate image.

The invention is based on the idea that virtual detection data, which are used for reconstructing an image, can be determined by forward projecting through an intermediate image. The forward projecting may be performed, for example, by using an acquisition geometry comprising a virtual desired trajectory along which a virtual irradiation unit moves relative to the field of interest during forward projecting. This virtual trajectory may be any arbitrary trajectory. The virtual detection data, which correspond to the virtual acquisition geometry and, in particular, to the virtual trajectory, are used for reconstructing an image of the field of interest. Therefore, the reconstruction process is not limited by the run of the first and the second trajectory, because the imaging system determines desired virtual detection data, which are used for reconstruction.

It is preferred that the first trajectory is arranged within a plane that intersects the field of interest and that the second trajectory is arranged at least partially outside said plane. If both trajectories were located within the same plane, only the portion of the field of interest situated in this plane could be reconstructed exactly, i.e. with high quality. Since the second trajectory is arranged at least partially outside the plane in this embodiment, a portion of this field of interest not situated within the plane can also be reconstructed exactly.

It is preferred that the moving unit is adapted such that the first trajectory is a circular trajectory. It is further preferred that the moving unit is adapted such that the second trajectory is a helical trajectory. These trajectories can be easily performed by imaging systems, wherein the irradiation unit and the field of interest are rotated relative to each other. These trajectories can be easily performed by CT systems, for example, because these trajectories can be performed without stopping the rotational movement, for example, of the irradiation unit relative to the field of interest.

In accordance with the invention, the helical trajectory may also be a portion of a helical trajectory, and the circular trajectory may also be a portion of a circular trajectory.

In an embodiment, the reconstruction unit is adapted such that only first detection data which correspond to one or several sections on the first trajectory are used for reconstructing the image of the field of interest. This means that these first detection data and the virtual detection data are used for reconstructing the image of the field of interest. The use of only these first detection data renders it possible to choose detection data which yield reconstructed images having fewer artefacts, i.e. having a high quality. For example, if moving elements are present within the field of interest, only the first detection data may be used for reconstruction, which data were acquired while the movement of these moving elements was relatively slow or while these moving elements did not move at all. Furthermore, if the moving elements move, for example, periodically, the first detection data used for reconstruction may be chosen such that the moving elements are always in the same moving phase while these first detection data are being acquired. The moving elements are preferably the moving parts of a heart.

It is further preferred that the forward-projection unit is adapted such that the forward projection is done along a virtual trajectory arranged such that it matches the first detection data which are used to reconstruct the image of the field of interest, so as to obtain complete data for reconstructing the image of the field of interest. Since complete data are obtained in this embodiment, an image of the field of interest can be reconstructed exactly, which leads to the reconstruction of a high-quality image.

It is further preferred that the forward-projection unit is adapted such that the virtual trajectory is arranged such that it intersects the plane at the one or several sections on the first trajectory. Furthermore, it is preferred that the forward-projection unit is adapted such that the virtual trajectory is arranged such that it intersects the plane at an endpoint of the one or several sections on the first trajectory. It is also preferred that the forward-projection unit is adapted such that the virtual trajectory is a line perpendicular to the plane. These virtual trajectories further improve the quality of the reconstructed images.

It is further preferred that the reconstruction unit is adapted such that the first detection data, which are used to reconstruct the image of the field of interest, are short-scan data. Short-scan data are data which cover less than a full rotation of the gantry. For example, if a first trajectory is a circular trajectory and if the imaging system is a CT system, short-scan data comprise data such that, seen from each object point to be reconstructed, each of these object points is irradiated by rays covering an angular range between 180° and 360° along the circular trajectory, i.e. the short-scan data correspond, for example, to a movement of an irradiation unit along a section of the circular trajectory having an angular width of 180° plus fan angle. The use of short-scan data is particularly useful if moving elements have to be reconstructed, because data of a small time window are used, i.e. the temporal resolution is increased.

It is also preferred that the reconstruction unit is adapted such that the first detection data, which are used to reconstruct the image of the field of interest, comprise several short-scan data sets, wherein different short-scan data sets correspond to different sections on the first trajectory. This renders it possible to use overscan data for reconstructing the image, yielding an improved signal-to-noise ratio and, therefore, a further improved image quality.

It is also preferred that the reconstruction unit is adapted such that reconstructing the intermediate image comprises the following steps:

reconstructing voxels of the intermediate image which have not been irradiated over an angular range of 360° along the first trajectory by using the second detection data, reconstructing voxels of the intermediate image which have been irradiated over an angular range of 360° along the first trajectory by using the first detection data and the second detection data.

Since voxels of the intermediate image which have been irradiated over an angular range of 360° along the first trajectory are reconstructed from not just the second detection data, but also from the first detection data, the quality of the reconstructed intermediate image is further improved, which results in a further improvement of the final reconstructed image. In another embodiment, only the second detection data can be used for reconstructing the intermediate image.

It is also preferred that the reconstruction unit is adapted for exactly reconstructing at least one of the intermediate image and the image of the field of interest which is reconstructed from the first detection data and the virtual detection data. Since the intermediate image and/or the final image are reconstructed exactly, the quality of these images is further improved.

In a further aspect of the present invention, an image generation device for generating an image of a field of interest is provided, the image generation device being provided with first detection data detected by a detection unit when an irradiation unit emitting radiation for irradiating the field of interest is moved relative to the field of interest along a first trajectory, the first detection data being dependent on the radiation after passing through the field of interest, and the image generation device being provided with second detection data detected by the detection unit when the irradiation unit is moved relative to the field of interest along a second trajectory, the second detection data being dependent on the radiation after passing through the field of interest, comprising:

a reconstruction unit for reconstructing an intermediate image of the field of interest from at least the second detection data and for reconstructing an image of the field of interest from the first detection data and virtual detection data, a forward-projection unit for determining the virtual detection data by forward projection of the intermediate image.

In a further aspect of the invention an imaging method for imaging a field of interest is provided, comprising the steps of:

irradiating the field of interest by means of an irradiation unit that emits radiation, moving the irradiation unit relative to the field of interest along a first trajectory and along a second trajectory by means of a moving unit, detecting first detection data depending on the radiation after passing through the field of interest when the irradiation unit is moved along the first trajectory, and detecting second detection data depending on the radiation after passing through the field of interest when the field of interest is irradiated along the second trajectory, by means of a detection unit, reconstructing an intermediate image of the field of interest from at least the second detection data by means of a reconstruction unit, determining the virtual detection data by forward projecting through the intermediate image by means of a forward-projection unit, reconstructing an image of the field of interest from the first detection data and virtual detection data by means of the reconstruction unit.

In a further aspect of the invention, an image generation method for generating an image of a field of interest is provided, the image generation method using first detection data detected by a detection unit when an irradiation unit emitting radiation for irradiating the field of interest is moved relative to the field of interest along a first trajectory, the first detection data being dependent on the radiation after passing through the field of interest, and the image generation method using second detection data detected by the detection unit when the irradiation unit is moved relative to the field of interest along a second trajectory, the second detection data being dependent on the radiation after passing through the field of interest, comprising the steps of:

reconstructing an intermediate image of the field of interest from at least the second detection data by means of a reconstruction unit, determining virtual detection data by forward projection of the intermediate image by means of a forward projection unit, reconstructing an image of the field of interest from the first detection data and the virtual detection data by means of the reconstruction unit.

In a further aspect of the invention, a computer program for imaging a field of interest is provided, comprising program code means for causing an imaging system to carry out the steps of the method as claimed in claim 15 when the computer program is run on a computer that controls an imaging system as claimed in claim 1 or 2.

In a further aspect of the invention, a computer program for generating an image of a field of interest is provided, comprising program code means for causing a computer to carry out the steps of the method as claimed in claim 16 when the computer program is run on a computer that controls an image generation device as claimed in claim 14.

BRIEF DESCRIPTION OF THE DRAWINGS

These and other aspects of the invention will be apparent from and elucidated with reference to the embodiments described hereinafter. In the following drawings FIG. 1 diagrammatically shows an embodiment of an imaging system in accordance with the invention.

FIG. 20 shows a projection of a first trajectory, which is a circular trajectory on the planar detector, FIG. 21 shows a projection of the circular trajectory on the planar detector, FIGS. 22 and 23 show filter lines with filter directions from left to right according to a filtered back-projection method in accordance with the invention, and FIGS. 24 and 25 show filter lines with filter directions from right to left according to a filtered back-projection method in accordance with the invention.

DETAILED DESCRIPTION OF EMBODIMENTS

Figure 1:
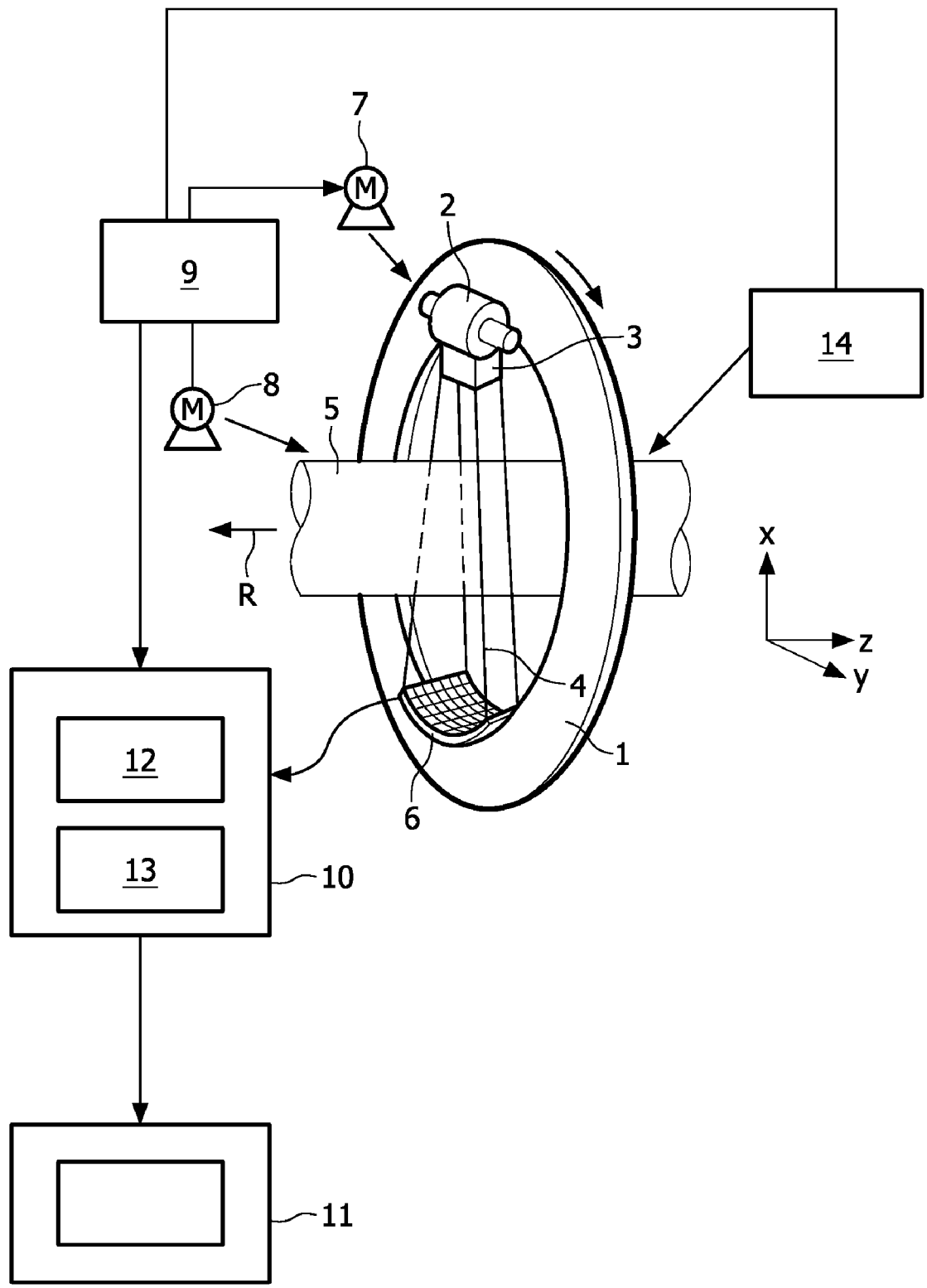

FIG. 1 shows an imaging system, a CT system in this embodiment. The CT system includes a gantry 1 which is capable of rotation about an axis of rotation R which extends parallel to the z-direction. The irradiation unit 2, an X-ray tube 2 in this embodiment, is mounted on the gantry 1. The X-ray tube is provided with a collimator device 3, which forms a conical radiation beam 4 from the radiation generated by the X-ray tube 2. The radiation traverses an object (not shown), such as a patient, in a field of interest in a cylindrical examination zone 5. After having traversed the examination zone 5, the X-ray beam 4 is incident on an X-ray detection unit 6, which is a two-dimensional detector mounted on the gantry 1 in this embodiment.

The gantry 1 is driven at a preferably constant, but adjustable angular speed by a motor 7. A further motor 8 is provided for displacing the object, e.g., a patient who is arranged on a patient table in the examination zone 5, parallel to the direction of the axis of rotation R or the z-axis. These motors 7, 8 are controlled by a control unit 9, for example such that the irradiation unit 2 and the examination zone 5 move relative to each other along a helical trajectory. However, it is also possible that the object or the examination zone 5 is not moved, but that only the X-ray tube 2 is rotated, i.e., that the irradiation unit 2 and the examination zone 5 move relative to each other along a circular trajectory. In this embodiment, the X-ray tube 2 is moved along a first, circular trajectory and along a second, helical trajectory.

The motors 7, 8, the gantry 1, and preferably a patient table form a moving unit in this embodiment.

First detection data are acquired when the X-ray tube 2 travels along the first trajectory, and second detection data are acquired when the X-ray tube 2 travels along the second trajectory. These detection data are acquired by the detection unit 6.

The data acquired by the detection unit 6 are provided to an image generation device 10 for image processing, in particular for reconstructing an image of the field of interest. The reconstructed image can finally be provided to a display 11 for displaying the image. Also, the image generation device 10 is preferably controlled by the control unit 9. Alternatively or in addition, the image generation device 10 may comprise a control unit for controlling the image generation device 10 only.

The image generation device 10 comprises a forward-projection unit 12 and a reconstruction unit 13. The reconstruction unit 13 is adapted for reconstructing an intermediate image of the field of interest using at least the second detection data. The forward-projection unit 12 is adapted for determining virtual detection data by forward projecting through the intermediate image. Any virtual trajectory, on which the X-ray source 2 virtually travels, may be used during forward projecting. The reconstruction unit 13 reconstructs a final image of the field of interest from the first detection data and the virtual detection data.

In this embodiment, the imaging system further comprises a unit 14 for determining motion within the field of interest. If the field of interest comprises moving elements, the unit 14 generates moving values corresponding to the movement of the moving elements within the field of interest. The unit 14 is, for example, an electrocardiograph, which is connected to a patient present in the field of interest, wherein, in particular, the heart of the patient is present within the field of interest. The moving values generated by the unit 14 are transferred to the image generation device 10, which can use the moving values for improving the quality of the reconstructed images. This will be explained in more detail further below.

The unit 14 for determining motion within the field of interest is preferably also controlled by the control unit 9. The moving values may be transferred to the image generation device 10 directly or via the control unit 9.

Figure 2:
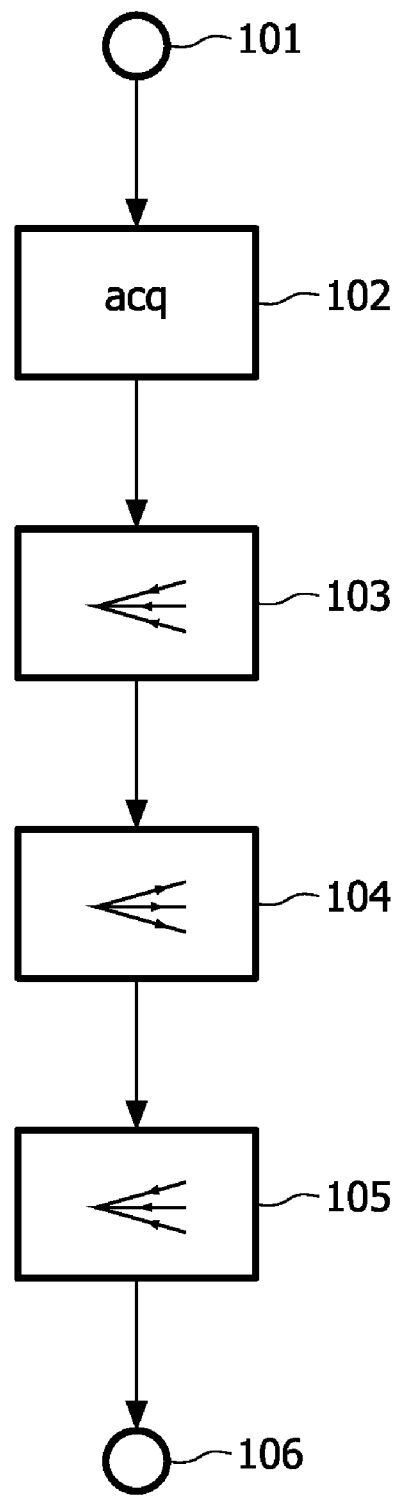
FIG. 2 is a flowchart illustrating an embodiment of an imaging method for imaging a field of interest in accordance with the invention, FIG. 3 diagrammatically shows a first trajectory and a second trajectory along which an irradiation unit of the imaging system travels.

An embodiment of a method for imaging a field of interest in accordance with the invention will now be described in more detail with reference to a flowchart shown in FIG. 2.

After initialization of the imaging system in step 101, first detection data and second detection data are acquired in step 102. In order to acquire first detection data, the X-ray tube 2 rotates around the field of interest, and the field of interest or the object is not moved, i.e. the X-ray tube 2 travels along a circular trajectory around the field of interest. In order to acquire the second detection data, the X-ray tube 2 rotates around the field of interest, and the field of interest or the object is moved parallel to the z direction, i.e. the X-ray tube 2 travels along a helical trajectory. These two trajectories can be performed by the imaging system by constantly rotating the X-ray tube 2 around the axis of rotation R and by modifying the movement of the field of interest or the object parallel to the z direction. The field of interest or the object can be moved by moving, for example, a patient table on which the object, for example, a patient, is located. The rotation of the X-ray tube 2 has not been modified, i.e., both trajectories can be performed, while the X-ray tube 2 rotates with constant angular speed.

Figure 3:
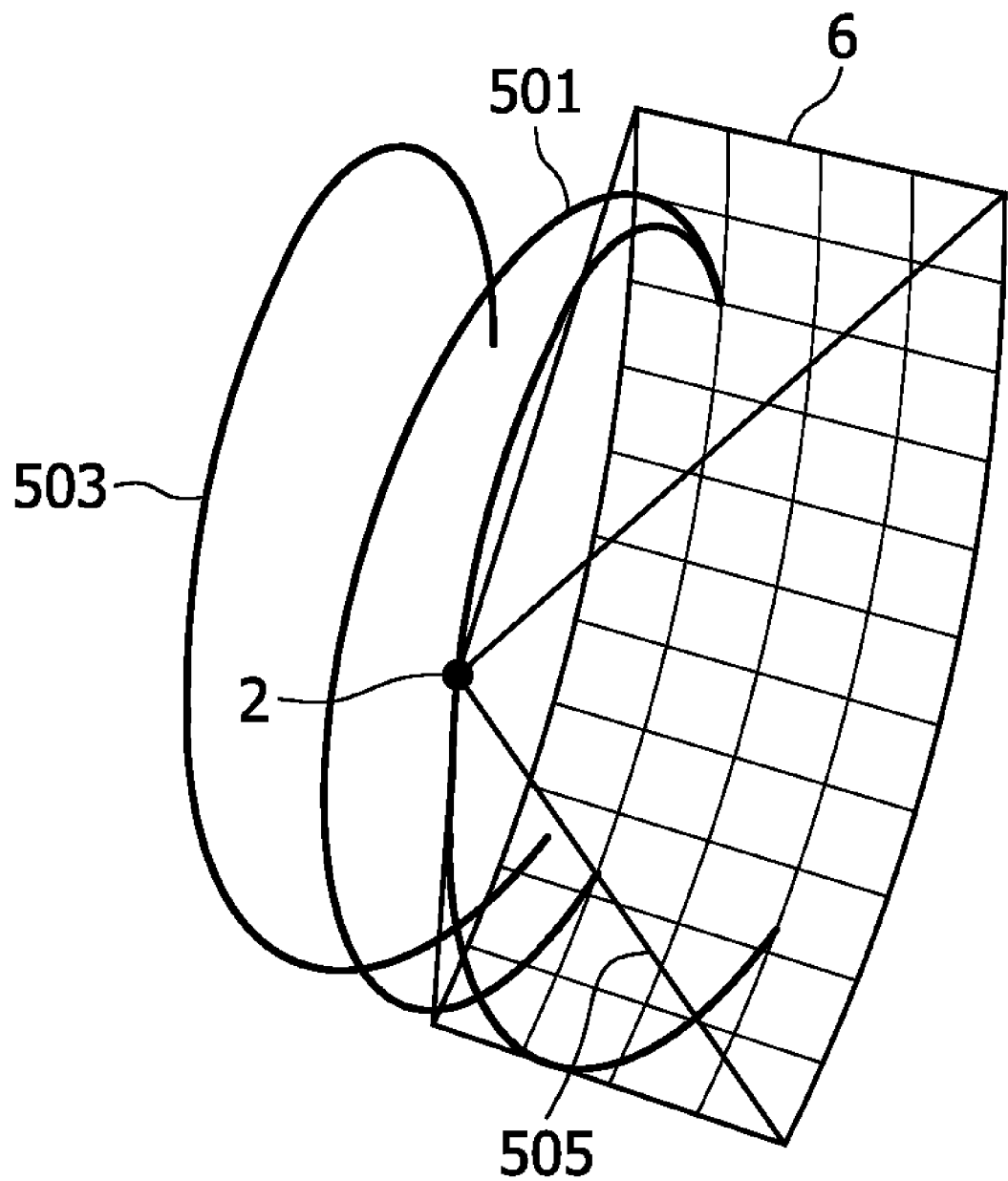

FIG. 3 shows schematically a first trajectory 501 being in this embodiment a circular trajectory and a second trajectory 503 being in this embodiment a helical trajectory. The irradiation unit 2 travels along these trajectories 501, 503.

It is preferred that in step 102 moving values are also acquired by the unit 14 for determining motion within the field of interest. The moving values are, for example, electrocardiograms which are transferred from the unit 14 to the image generation device 10. The first detection data and the second detection data are also transferred to the image generation device 10.

In step 103, the reconstruction unit 13 of the image generation device 10 reconstructs an intermediate image of the field of interest from at least the second detection data. In particular, an X-ray reconstruction algorithm is used to reconstruct the intermediate image. For example, if the second trajectory is a helical trajectory, the intermediate image is preferably reconstructed by the method described in "EnPiT: Filtered Back-Projection Algorithm for Helical CT Using an n-Pi Acquisition" by C. Bontus, et. al., IEEE Trans. Med. Imaging 24, 977-986 (2005). Other known reconstruction algorithms may also be used to reconstruct the intermediate image, for example, filtered back-projection algorithms may be used to reconstruct the intermediate image.

Figure 4:
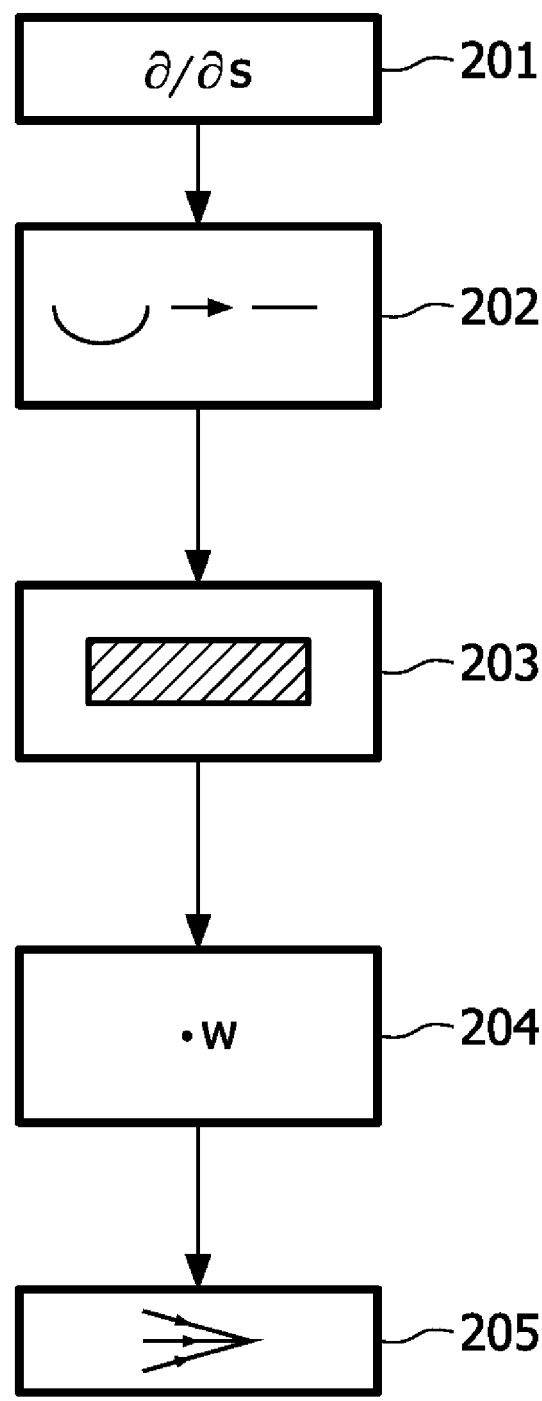
FIG. 4 is a flowchart illustrating a reconstruction of an intermediate image in accordance with the invention.

In step 103 for reconstructing the intermediate image, it is preferred that, if the second trajectory is a helical trajectory and if the first trajectory is a circular trajectory, a reconstruction of the helical or second detection data by an exact helical method, for example as described in the cited article by C. Bontus, et al., is applied only to object points which have not been irradiated over an angular interval of 360° along the circular or first trajectory. Object points irradiated over an angular interval of 3600 along the circular or first trajectory are preferably reconstructed in step 103 using a full-scan circle and helix reconstruction. A preferred full-scan circle and helix reconstruction will be described below with reference to a flowchart shown in FIG. 4.

In step 201, the detected data are differentiated. In order to explain this differentiation, the preferred acquisition process will first be described mathematically.

The measured projection data $D_f$ can be described by following equation for every position y on the first or second trajectory:

$$D_f(y, \Theta) = \int_0^\infty dl f(y + l\Theta) \tag{1}$$

In other words, from every position y on the first or second trajectory, line integrals along rays which traverse the field of interest f(x) and which are detected by the detection unit 6 are considered, the unit vector $\Theta$ pointing in the directions of the respective rays.

The differentiation of the first and second detection data in step 201 is preferably performed in accordance with the following equation:

$$D'_f(y(s), \Theta) = \frac{\partial D_f(y(s), \Theta = const.)}{\partial s} \tag{2}$$

The variable s parameterizes different positions on the first and the second trajectory.

Detected data values which correspond to parallel X-rays emanating from different focal spot positions are thus differentiated. This differentiation step may be performed using a Fourier filter. This differentiation is performed separately for the circular trajectory and the helical trajectory, which may be a portion of a helical trajectory, and is explained in more detail in "A quasiexact reconstruction algorithm for helical CT using a 3-Pi acquisition" by C. Bontus et al., Med. Phys. 30, 2493-2502 (2003).

In step 202, a virtual planar detector 605 is defined, which is described in the above-mentioned reference "A quasiexact reconstruction algorithm for helical CT using a 3-Pi acquisition" by Bontus, C. et al., Med. Phys. 30, 2493-2502 (2003). The virtual planar detector contains the rotational axis R. Coordinates on this detector are denoted $u_{PL}$ and $v_{PL}$, wherein the $v_{PL}$-axis is parallel to the z-axis. A line is considered containing the source and being perpendicular to the virtual planar detector. The point ($u_{PL}=0$, $v_{PL}=0$) corresponds to the point at which this line intersects the planar detector.

Figure 5:
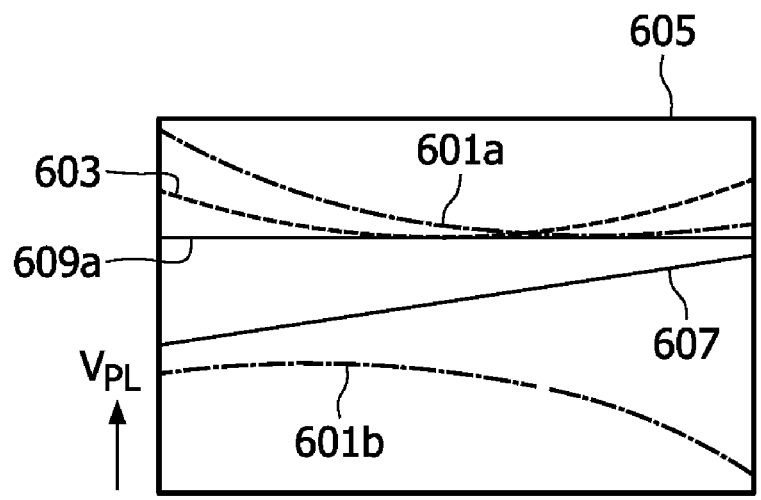
FIGS. 5 to 8 show projections of trajectories an a planar detector.
Figure 6:
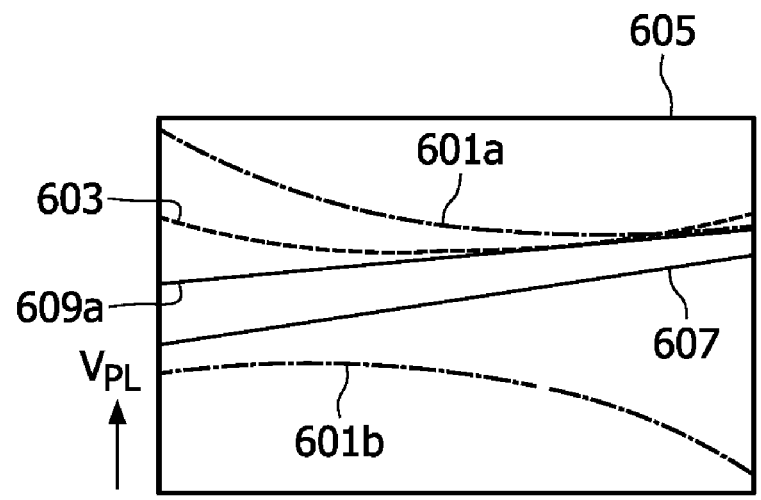
Figure 7:
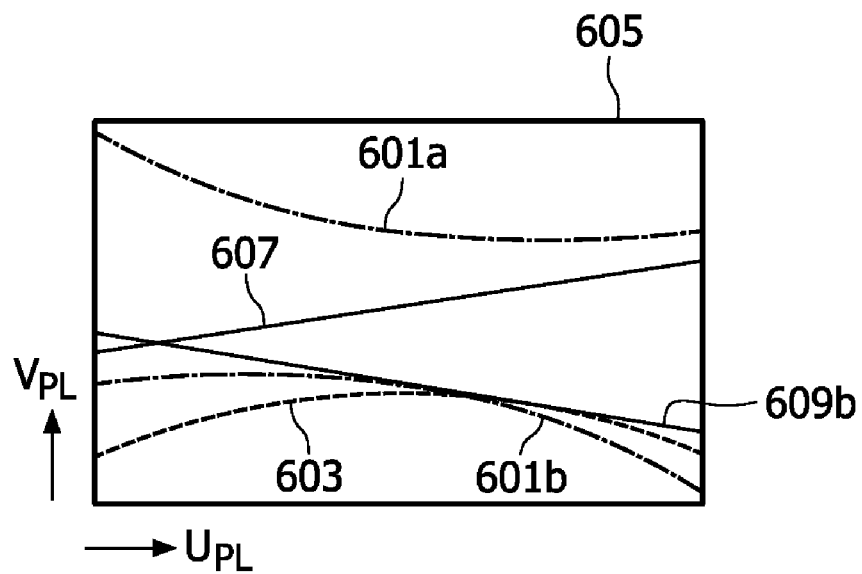

Furthermore, the circular 501 and the helical 503 trajectory are projected along the corresponding X-rays 505 onto the virtual planar detector, only the four outermost X-rays being illustrated in FIG. 3, which shows a focus centered detector. The projection 603 of the circular trajectory 501 and the projections 601a, 601b of the helical trajectory 503 are shown in FIGS. 5 to 7, seen from a focal spot position on the helical trajectory 503. From FIG. 5 to FIG. 7 the focal spot moves on the helical trajectory 503, i.e. the projections 603, 601a, 601b are seen from different focal spot positions, the focal spot being positioned on one side of the circular position in FIG. 5, the focal spot being positioned on the same side of, but closer to the circular position in FIG. 6, and the focal spot being positioned on the other side of the circular position in FIG. 7.

Two turns of the helical trajectory 503 are projected onto the planar detector 605. Thus, FIGS. 5 to 7 show two projections 601a, 601b of turns of the helical trajectory 503. The line 603 is the projection of the circular trajectory 501.

The projection 603 of the circular trajectory 501 can be parameterized according to the following equation:

$$v_{Pl}(u_{Pl}) = -\frac{z_0}{2}\left[1 + \left(\frac{u_{Pl}}{R}\right)^2\right]. \tag{3}$$

Equation (3) describes a projection seen from a source at $z=z_0$. R corresponds to the distance from the source, for example the focal spot of the X-ray tube 2, to the rotational axis.

The projections 601a, 601b of the turns of the helical trajectory 503 on the planar detector 605 can be parameterized according to the following equation:

$$v_{Pl}^{up,low}(u_{Pl}) = \pm h\left(1 + \left(\frac{u_{Pl}}{R}\right)^2\right)\left(\frac{\pi}{2} \mp arctan\frac{u_{Pl}}{R}\right), \tag{4}$$

wherein $v_{Pl}^{up}(u_{Pl})$ defines the upper projection 601a of the turns of the helical trajectory 503 and wherein $v_{Pl}^{down}(u_{Pl})$ defines the lower projection 601b of the turns of the helical trajectory 503. The algebraic sign "+" corresponds to $v_{Pl}^{up}(u_{Pl})$, and the algebraic sign "−" corresponds to the $v_{Pl}^{low}(u_{Pl})$.

The solid line 607 passes the center of the planar detector 605 and is the asymptote, which has a positive gradient, to the projections 601a, 601b of the helical trajectory 503. The solid lines 609a, b are the tangents to the projection 603 of the circular trajectory and to the upper projection 601a and to the lower the projection 601b of the helical trajectory 503, respectively, depending on the position of the focal spot relative to the circular position. That is, if the projection 603 of the circular trajectory is located in the upper part of the planar detector 605 (FIGS. 5 and 6, $z_0<0$), the solid line 609a is the tangent to the projection 603 of the circular trajectory and to the upper projection 601a of the helical trajectory 503, and if the projection 603 of the circular trajectory is located in the lower part of the planar detector 605 (FIG. 7, $z_0>0$), the solid line 609b is the tangent to the projection 603 of the circular trajectory and the lower projection 601b of the portion 503 of the helical trajectory, wherein, in this embodiment, the circular trajectory is located at z=0.

Figure 8:
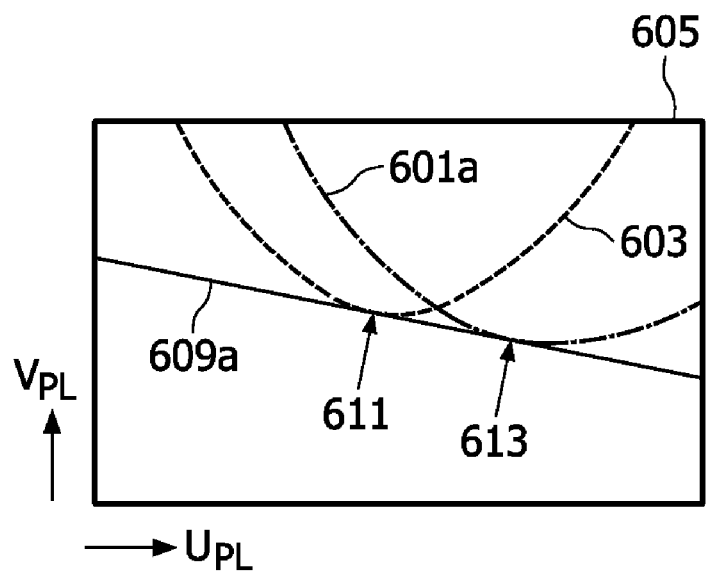

FIG. 8 shows the upper portion of FIG. 5 on a larger scale.

The helically detected data values and the circularly detected data values, i.e. the second detection data and the first detection data, are projected onto the planar detector 605 along the corresponding X-rays.

In step 203, the helically detected data and the circularly detected data are filtered along filter lines using a $1/\sin\gamma$ filter. The filter lines for this are determined first. They depend on the position of the focal spot and the object point to be reconstructed. Denoting the position of the object-point as x and the position of the source as y(s), wherein s is an angular parameter, the following equation defines the unit vector b:

$$b(s, x) = \frac{x - y(s)}{|x - y(s)|}. \quad (5)$$

That is to say, b points from the source to the object-point. The filter directions, which are defined as the directions along filter lines, can be characterized by unit vectors e which are perpendicular to b. The relationship between e-vectors and filter lines, and directions along the filter lines, is described in the appendix of "A quasiexact reconstruction algorithm for helical CT using a 3-Pi acquisition" by C. Bontus et al., Med. Phys. 30, 2493-2502 (2003), which is incorporated herein by reference. For every s and for every x, there may be one or more filter directions which have to be used.

Using b and e, the filtering step can be described by the following equation in this embodiment:

$$P(s, b) = \sum_{q=1}^{N_f} \mu_q \int_{-\pi}^{\pi} \frac{d\gamma}{\sin\gamma} D'_f(y(s), \cos\gamma b + \sin\gamma e_q). \quad (6)$$

The summation over q in equation (6) is performed because there may be more than one filter direction, i.e. more than one filter line and corresponding direction along the filter line for each detected data value, each detected data value corresponding to a combination of s and b. A definition of the vectors e is crucial for the described embodiment. Once the filtered data have been obtained, a back-projection step can be performed.

Certainly, the described procedure has to be applied separately to the circular trajectory 501 and to the helical trajectory 503. In particular, y(s) corresponds to either the circular trajectory or the helical trajectory in this embodiment. Finally, the results of the back-projection step 205, which will be described further below, are added up.

The filter lines of the circularly detected data are defined according to the following equation:

$$v_{Pl}(u_{Pl}) = v_0 + \sigma u_{Pl} \quad (7)$$

Thus, the filter lines correspond to straight lines on the planar detector. In general, the gradient σ is different for different filter lines, but in this embodiment the gradient σ is identical for all filter lines of circularly detected data, i.e. these filter lines are parallel to each other. Furthermore, the circularly detected data are filtered along filter lines which are parallel to the $u_{Pl}$-axis, i.e. $v_{Pl}(u_{Pl}) = v_0$ in this embodiment. The different filter lines are parameterized by $v_0$.

The filter direction goes from left to right along the respective filter lines in the orientation shown in FIGS. 9 to 12. The orientation refers to a right-handed coordinate system wherein the $u_{Pl}$-axis is the first axis, wherein the $v_{Pl}$-axis is the second axis, and wherein the third axis points in the direction from the center of the planar detector towards the X-ray source. The $u_{Pl}$-axis points from left to right. The $v_{Pl}$-axis points from the bottom to the top. In this description the terms "left", "right", "above", "below", "positive gradient", "negative gradient" etc. refer to this right-handed coordinate system.

The filter lines and helically detected data, which will be ignored during reconstruction of the intermediate image in this embodiment, will first be explained with reference to situations in which the focal spot is positioned on the side of the circular position as illustrated by FIGS. 5, 6, 8, i.e. in which the projection 603 of the circular trajectory is located in the upper part of the virtual planar detector. If the circular position is located at $z_0=0$, these situations illustrated in FIGS. 5, 6, 8 correspond to $z_0<0$.

Helically detected data which are projected onto certain regions on the planar detector are not used for reconstruction and are therefore not filtered. These regions comprise all points on the planar detector lying above the projection 603 of the circle, all points lying above the upper projection 601a of the portion 501 of the helical trajectory, and all points with $u_{Pl}$-coordinates between two points of tangency 611, 613 (see FIG. 8) of the tangent 609a, which is tangential to the projection 603 of the circular trajectory 501 and to the upper projection 601a of the helical trajectory 503, and which are located above this tangent 609a.

Two sets of filter lines are defined for the helically detected data, i.e. for helically detected data in equation (6) $N_f$ is equal to 2 in this embodiment.

A first set of filter lines for helically detected data is determined as follows. For a helically detected data value whose projection on the planar detector 605 is located below the asymptote 607, the corresponding filter line is parallel to the asymptote 607, i.e. parallel to the derivative $\dot{y}_h(s)$ of the helical trajectory 503, wherein the helical trajectory is denoted $y_h(s)$. If the projection of the helically detected data value is located above the asymptote 607, the corresponding filter line is either tangential to the projection 603 of the circular trajectory 501 or tangential to the upper projection 601a of the helical trajectory 503, the point of tangency being located on the right-hand side of the location of the projection of the corresponding helically detected value on the planar detector 605. The decision whether the filter lines are tangential to the projection 603 of the circular trajectory 501 or tangential to the upper projection 601*a* of the helical trajectory 503 depends on the gradients of the corresponding tangents. If the gradient of the corresponding tangent of the projection 603 of the circular trajectory 501 is smaller than that of the tangent of the upper projection 601*a* of the helical projection 503, the filter line is tangential to the projection 603 of the circular trajectory 501. If the gradient of the corresponding tangent of the projection 603 of the circular trajectory 501 is greater than that of the tangent of the upper projection 601*a* of the helical projection 503, the filter line is tangential to the upper projection 601*a* of the helical trajectory 503.

The respective tangents run through the respective detected data value for which a filter line has to be determined. Thus, the gradient of the respective tangent is defined by the position of the projected helically detected data value on the planar detector.

The algebraic sign is considered in the comparison of gradients. Thus, a negative gradient with a greater absolute value is smaller than a negative gradient having a smaller absolute value.

The helically detected data are filtered from the left to the right along the filter lines of the first set of filter lines.

Figures 9, 10:
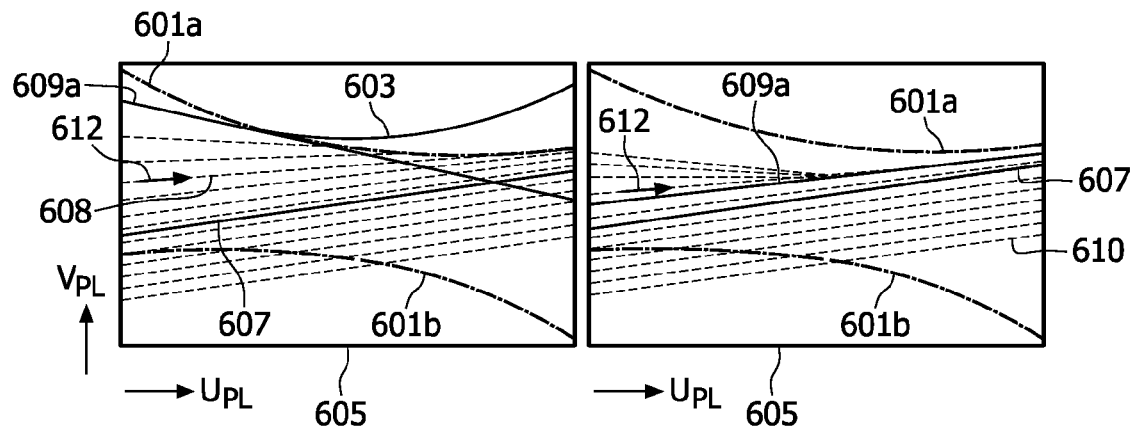
FIGS. 9 to 12 show filter lines on the planar detector.

A first set of filter lines 608, 610 is shown in FIGS. 9 and 10 for two different focal spot positions on the helical trajectory, wherein $z_0$ is negative. The helically detected values, projected onto the virtual planar detector are filtered along the filter lines 608, 610 from left to right, i.e. in the direction indicated by the arrows 612.

A second set of filter lines is determined as follows. For a helically detected data value which has been projected onto the planar detector 605 the corresponding filter line is either tangential to the projection 603 of the circular trajectory 501 or tangential to the upper projection 601*a* of the helical trajectory 503, the point of tangency being located on the left-hand side of the location of the projection of the corresponding helically detected value on the planar detector 605. The decision whether the filter lines are tangential to the projection 603 of the circular trajectory 501 or tangential to the upper projection 601*a* of the helical trajectory 503 depends on the gradients of the corresponding tangents. If the gradient of the corresponding tangent of the projection 603 of the circular trajectory 501 is smaller than that of the tangent of the upper projection 601*a* of the helical projection 503, the filter line is tangential to the upper projection 601*a* of the helical trajectory 503. If the gradient of the corresponding tangent of the projection 603 of the circular trajectory 501 is greater than that of the tangent of the upper projection 601*a* of the helical projection 503, the filter line is tangential to the projection 603 of the circular trajectory 501.

The helically detected data are filtered from the right to the left along the filter lines of the second set of filter lines.

Figures 11, 12:
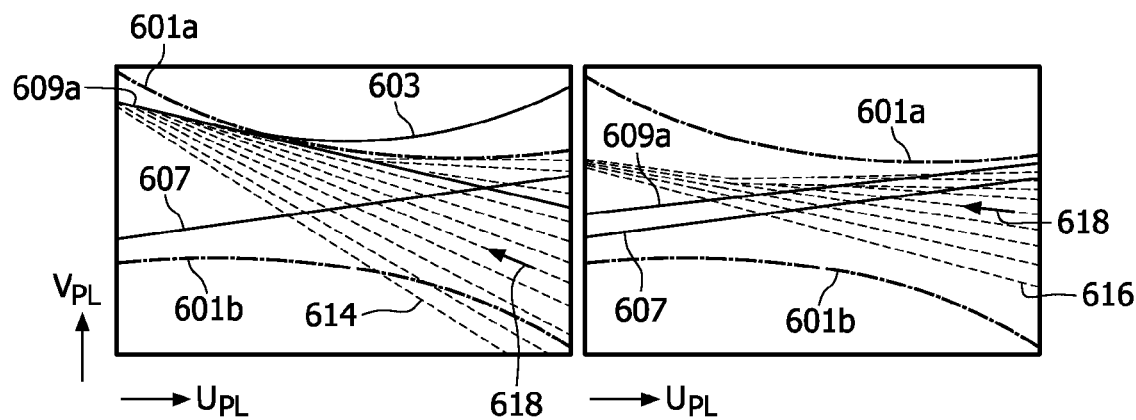

A second set of filter lines 614, 616 is shown in FIGS. 11 and 12 for two different focal spot positions on the portion of the helical trajectory, wherein $z_0$ is negative. The helically detected values projected onto the virtual planar detector are filtered along the filter lines 614, 616 from right to left, i.e. in the direction indicated by the arrows 618.

Above, the filter lines and the ignored helically detected data, i.e. the helically detected data not filtered which will not be back-projected further below, are described for helically detected data whose corresponding focal spot position is located on a side of the circular position which corresponds to the situations illustrated in FIGS. 5, 6, 8, i.e. for $z_0<0$. The above description of the filter lines can be analogously applied to situations in which the focal spot is located on the opposite site of the circular position, i.e. for $z_0>0$, wherein the terms "upper projection 601*a* of the helical trajectory 503" or the like has to be substituted by "lower projection 601*b* of the helical trajectory 503". Furthermore, the terms "upper", "above" etc. have to be substituted by "lower", "below" etc. and vice versa.

In particular, a first set of filter lines for helically detected data for $z_0>0$ is determined as follows. For a helically detected data value whose projection on the planar detector 605 is located above the asymptote 607, the corresponding filter line is parallel to the asymptote 607, i.e. parallel to the derivative $\dot{y}_h(S)$ of the helical trajectory 503. If the projection of the helically detected data value is located below the asymptote 607, the corresponding filter line is either tangential to the projection 603 of the circular trajectory 501 or tangential to that of the lower projection 601*b* of the helical trajectory 503, the point of tangency being located on the left-hand side of the location of the projection of the corresponding helically detected value on the planar detector 605. The decision whether the filter lines are tangential to the projection 603 of the circular trajectory 501 or tangential to the lower projection 601*b* of the helical trajectory 503 depends on the gradients of the corresponding tangents. If the gradient of the corresponding tangent of the projection 603 of the circular trajectory 501 is smaller than that of the tangent of the lower projection 601*b* of the helical projection 503, the filter line is tangential to the projection 603 of the circular trajectory 501. If the gradient of the corresponding tangent of the projection 603 of the circular trajectory 501 is greater than that of the tangent of the lower projection 601*b* of the helical projection 503, the filter line is tangential to the lower projection 601*b* of the helical trajectory 503. The direction of filtering goes from left to right.

A second set of filter lines for $z_0>0$ is determined as follows. For a helically detected data value projected onto the planar detector 605, the corresponding filter line is either tangential to the projection 603 of the circular trajectory 501 or tangential to the lower projection 601*b* of the helical trajectory 503, the point of tangency being located on the right-hand side of the location of the projection of the corresponding helically detected value on the planar detector 605. The decision whether the filter lines are tangential to the projection 603 of the circular trajectory 501 or tangential to the lower projection 601*b* of the helical trajectory 503 depends on the gradients of the corresponding tangents. If the gradient of the corresponding tangent of the projection 603 of the circular trajectory 501 is smaller than that of the tangent of the lower projection 601*b* of the helical projection 503, the filter line is tangential to the lower projection 601*b* of the helical trajectory 503. If the gradient of the corresponding tangent of the projection 603 of the circular trajectory 501 is greater than that of the tangent of the lower projection 601*b* of the helical projection 503, the filter line is tangential to the projection 603 of the circular trajectory 501. The direction of filtering goes from right to left.

After determination of the filter lines and the corresponding directions along the filter lines, the detected data are filtered according to equation (6) using a $1/\sin \gamma$ filter.

A detected data value is parameterized by a combination of s and b, wherein for each circularly detected data value, i.e. for each first detection data value, one filter line is determined in this embodiment, and wherein for each helically detected data value, i.e. for each second detection data value, two filter lines are determined in this embodiment. If a filtered detected data value P(s, b) is determined for a combination of s and b and a corresponding filter line, the angle γ is the angle between the vector b and the vector pointing from the focal spot position to the different detected data values projected onto the planar detector on the corresponding filter line. Thus, the angle γ samples the different detected data values along the corresponding filter line. A more detailed description of this 1/sin γ filter is given in "A quasiexact reconstruction algorithm for helical CT using a 3-Pi acquisition" by C. Bontus et. al, Med. Phys. 30(9) pp. 2493-2502 (2003).

A filter line determined for a helically detected value projected onto the planar detector obviously runs through this projected helically detected value, which can be parameterized by a combination of s and b.

In step 204, the filtered detected data are weighted according to equation (6) with the weights $\mu_q$. The filtered helically detected data filtered along filter lines of the first set of filter lines are weighted with a value of one half. The filtered helically detected data filtered along filter lines of the second set of filter lines are also weighted with a value of one half. The filtered circularly detected data are weighted with a value of one.

In step 205, the weighted filtered helical data filtered along filter lines of the first set of filter lines, the weighted filtered helical data filtered along the filter lines of the second set of filter lines, and the weighted filtered circularly detected data are back-projected according to the following equation, wherein each data value is divided by the distance between the corresponding position y of the focal spot and the location x of the object of interest, i.e. the position of the voxel of the image that is to be reconstructed:

$$f(x) = \frac{(-1)}{2\pi^2} \int_I \frac{ds}{|x - y(s)|} P(s, b(s, x)). \qquad (8)$$

If all locations x of the object of interest have been reconstructed by back-projection, the intermediate image has been reconstructed.

Although the filter lines and directions along these filter lines have been defined here using projections on a virtual planar detector, the reconstruction of the intermediate image may alternatively be carried out without the use of this planar detector. This virtual planar detector is used only to illustrate the filter lines and the direction along these filter lines for the detected data values.

A multi-cycle cardiographic reconstruction is performed with the use of the first detection data, i.e. the circular data, for the reconstruction of object points within the field of interest which have been irradiated over an angular interval of 360°, using the above described full-scan circle and helix reconstruction.

Those projections which are closest to the selected phase point are preferred for the multi-cycle reconstruction. In particular, if the first projection data belong to a circle which is covered more than once, a weighted averaging of the projection data belonging to the same angular source position can be performed, resulting in projection data covering only a single circle. Here, the averaging should be performed such that projections closest to the selected phase point are given the highest weights. Such multi-cycle reconstructions are disclosed, for example, in "ECG Gated continuous circular cone-beam multi-cycle reconstruction for in-stent coronary artery imaging: A phantom study" by U. van Stevendaal et. al., Proc. SPIE vol. 6142 (2006).

The advantage of distinguishing between object points which have not been irradiated over an angular interval of 360° and object points which have been irradiated over an angular interval of 360° is that contrast agents, which may be present within the field of interest during the acquisition of the first detection data and which have not been present during the acquisition of the second detection data, cannot have an adverse effect and that the motion of the heart and the respiratory motion produce fewer artefacts in the reconstructed image of the field of interest.

In step 103, and in particular in steps 201 to 205, a reconstructed intermediate image of the field of interest is transferred to the forward-projection unit 12, which performs a forward projection through the intermediate image in step 104. The forward projection is performed in this embodiment by using a virtual trajectory along which the irradiation unit virtually travels. The first trajectory is a circular trajectory in this embodiment, and the first detection data are detection data acquired while the irradiation unit has been traveling over an angular range of 180° plus fan angle along the first trajectory, i.e. the first detection data are short-scan data in this embodiment. The virtual trajectory in this embodiment is a line parallel to the z axis and intersecting the first trajectory at one of the end points of a section along the first trajectory, which covers an angular range of 180° as seen from the respective object point, which has to be reconstructed. This angular range of 180° is indicated below by the term "back-projection interval". In other embodiments, the back-projection interval may correspond to a different angular range of short-scan data.

Preferably, a back-projection interval and a virtual trajectory are determined for each object point which has to be reconstructed, i.e. for each point within the field of interest, and a forward-projection along the respective virtual trajectory is performed. The relation between the back-projection interval on the first trajectory and the virtual line is diagrammatically shown for a point 26 within the field of interest in FIG. 13.

Figure 13:
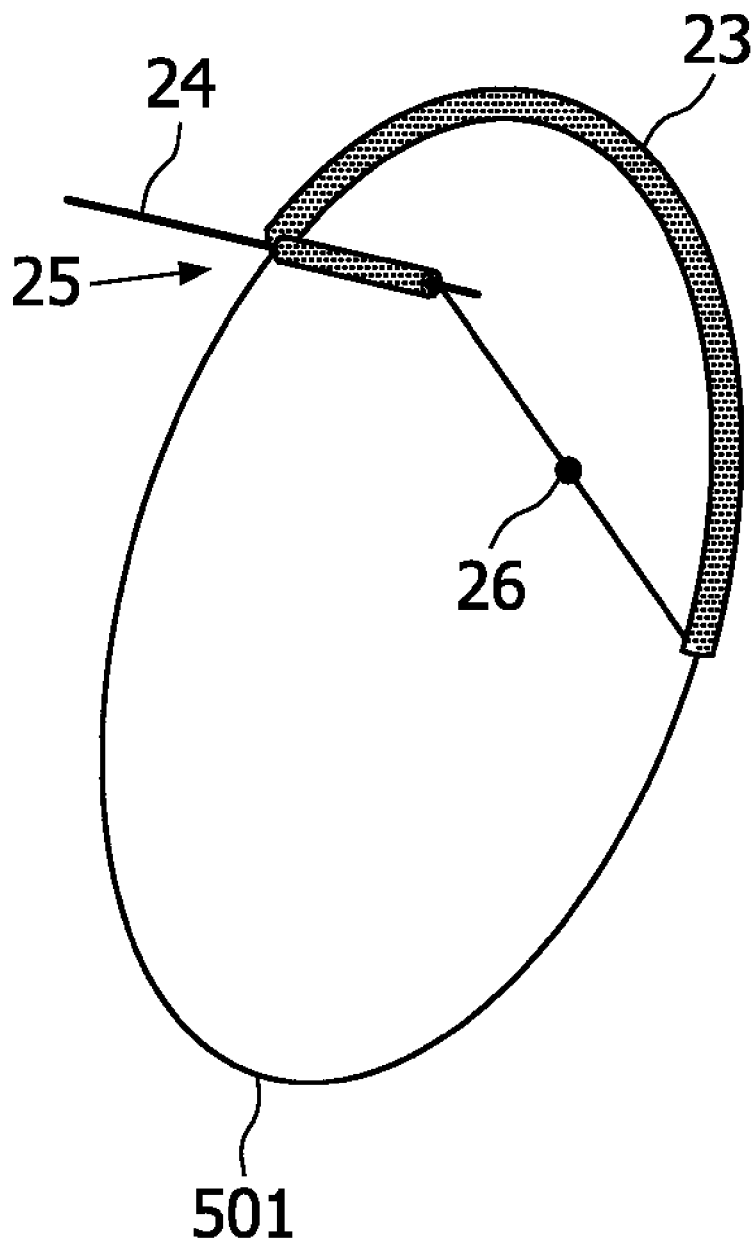
FIG. 13 diagrammatically shows the first trajectory and a virtual trajectory.

FIG. 13 shows the first trajectory 501 and a back-projection interval 23 on the first trajectory 501. The virtual trajectory 24 runs parallel to the z-axis and intersects the first trajectory 501 at the end point 25 of the back-projection interval 23. The location 26 within the field of interest is an exemplary location within the field of interest which can be reconstructed from first detection data, which correspond to the back-projection interval 23, and from virtual detection data, which are generated by forward projection through the intermediate image, while a virtual irradiation unit travels along the virtual line 24.

It is preferred that the back-projection interval is chosen such that moving elements within the field of interest, for example a human heart within the field of interest, have moved slowly during an acquisition of the first detection data, in particular have moved as slowly as possible. Furthermore, if the moving elements within the field of interest move periodically, in particular if the moving element within the field of interest is a human heart, it is preferred that several sets of first detection data are acquired or chosen for the reconstruction, such that the moving elements within the field of interest have been in the same moving phase during the acquisition of these several sets of first detection data. That is, known gating methods can be used, which are, for example, disclosed in "Cardiac Cone Beam CT" by R. Manzke, PhD Thesis, King's College London, September 2004. This document is incorporated by reference into the present document and can be obtained, for example, via ww.cardiac.net.

After virtual detection data have been determined by forward-projection through the intermediate image, while a virtual irradiation unit travels along a virtual trajectory, an image of the field of view is reconstructed in step 105 using the first detection data and the virtual detection data. Known standard reconstruction algorithms, for example a filtered back-projection algorithm, can be used for this final reconstruction. It is preferred, however, that the first trajectory is a circular trajectory and that the virtual trajectory is a line parallel to the z-axis, and that this final reconstruction is performed by using the circle-and-line reconstruction method to be described below.

This circle-and-line reconstruction method is a filtered back-projection method which will be described based on the circular trajectory and a linear virtual trajectory.

In the filtered back-projection method according to an embodiment of the invention, the circular trajectory is contained in the xy-plane and the virtual line is parallel to the z-axis. The latter will be denoted as a z-line. Points on this trajectory sequence can be parameterized according to equation (9):

$$y_0(s) = \begin{pmatrix} R\cos s \\ R\sin s \\ 0 \end{pmatrix}, \quad y_1(z) = \begin{pmatrix} R \\ 0 \\ z \end{pmatrix}. \tag{9}$$

In equation (9), R corresponds to the distance from the source to the rotational axis, and s is an angular variable parameterizing the trajectory.

In the following, an analysis of detector shapes will be described.

A conventional CT scanner usually contains a detector, which is part of a cylinder surface. The axis of symmetry of this cylinder may be parallel to the z-axis and may contain the focal spot. Points on such a "focus detector" can be parameterized using an angular variable $\alpha$ and a variable $v_F$. For a source located on the z-line at $z=z_0$, a vector $r_F$ pointing from the origin to the element on the focus detector is given by equation (10):

$$r_F(\alpha, v_F, z_0) = \begin{pmatrix} R - D\cos\alpha \\ D\sin\alpha \\ z_0 + v_F \end{pmatrix}. \tag{10}$$

In equation (10), D corresponds to the distance from the source to the detector center.

For convenience, a virtual "center detector" may be introduced. Similar to the focus detector, the center detector is located on the surface of a cylinder. The axis of symmetry of the cylinder corresponds to the z-axis now such that the points on the detector can be parameterized by introducing a vector $r_C$:

$$r_c(\beta, v_c, z_0) = \begin{pmatrix} -R\cos\beta \\ R\sin\beta \\ z_0 + v_C \end{pmatrix}. \tag{11}$$

Figure 14:
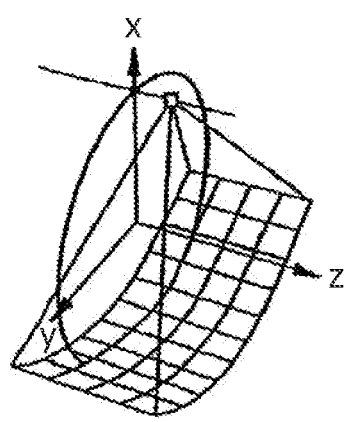
FIG. 14 diagrammatically shows a focus detector according to a filtered back-projection method in accordance with the invention, FIG. 15 diagrammatically shows a center detector according to a filtered back-projection method in accordance with the invention, FIGS. 16 and 17 diagrammatically show parallel rays parameterized by focus detector coordinates according to a filtered back-projection method in accordance with the invention, FIGS. 18 and 19 diagrammatically show parallel rays parameterized by center-detector coordinates according to a filtered back-projection method in accordance with the invention.
Figure 15:
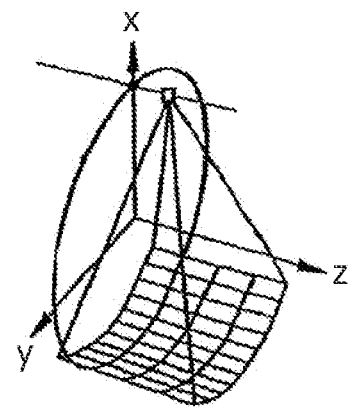

In equation (11), $\beta$ and $v_C$ are detector coordinates in complete analogy to the focus detector coordinates $\alpha$ and $v_F$. FIG. 14 and FIG. 15 exemplify the trajectory and the focus and center detector. Particularly, FIG. 14 shows the focus detector approach, whereas FIG. 15 shows the center detector approach.

The line containing the focal spot and a certain focus detector element can be parameterized as $l_F$, see equation (12):

$$l_F(\alpha, v_F, z_0, \sigma) = \begin{pmatrix} R \\ 0 \\ z_0 \end{pmatrix} + \sigma \begin{pmatrix} -D\cos\alpha \\ D\sin\alpha \\ v_F \end{pmatrix}, \quad 0 \le \sigma \le 1. \tag{12}$$

Using equation (12), the coordinates of the detector element onto which an object point $x=(x, y, z)$ is projected can be computed:

$$\tan\alpha = \frac{y}{R-x} \Rightarrow \tag{13}$$
$$\sigma = \frac{R-x}{D\cos\alpha} \Rightarrow$$
$$v_F = \frac{z-z_0}{\sigma}.$$

Similarly, the line containing the focal spot and a center detector element can be parameterized according to equation (14):

$$l_C(\beta, v_C, z_0, \sigma) = \begin{pmatrix} R \\ 0 \\ z_0 \end{pmatrix} + \sigma \begin{pmatrix} -R(1+\cos\beta) \\ R\sin\beta \\ v_C \end{pmatrix}, \quad 0 \le \sigma \le 1. \tag{14}$$

The object-point is projected onto the detector element with coordinates:

$$\tan\frac{\beta}{2} = \frac{y}{R-x} \Rightarrow \tag{15}$$
$$\sigma = \frac{R-x}{R(1+\cos\beta)}$$
$$= \frac{R-x}{2R\cos^2\frac{\beta}{2}} \Rightarrow$$
$$v_C = \frac{z-z_0}{\sigma}.$$

The coordinates $\alpha$ and $\beta$ depend only on x, y for the focus detector as well as for the center detector, whereas $v_F$ and $v_C$ depend on x, y, and z.

In the following, an analysis of parallel rays will be described.

A physical detector may comprise columns and rows. The corresponding detector elements may be equidistantly separated in the variables $\alpha$ and $v_F$. Therefore, equations (16) and (17) parameterize the centers of the detector elements for fixed $z=z_0$:

$$\alpha_k = \alpha_0 + k\Delta\alpha, \quad k=0, \ldots, \#\text{columns}-1, \tag{16}$$

$$v_{Fp} = v_{F0} + p\Delta v_F, \quad p=0, \ldots, \#\text{rows}-1. \tag{17}$$

It may be convenient for mathematical reasons to reorganize the data taken along the z-line before the back-projection is performed. Data from different source-positions may be combined for projection data associated with a parallel detector. If center detector coordinates are used, the parameterization of the coordinates in parallel geometry is given, for a fixed $v_C$, by equations (18), (19):

$$\beta_k = \beta_0 + k\Delta\beta, \ k=0,\ldots,\# \text{columns}-1, \quad (18)$$

$$z_{0,p} = z_{0,min} + p\Delta z, \ p=0,\ldots,\# \text{projections}-1. \quad (19)$$

Figure 16:
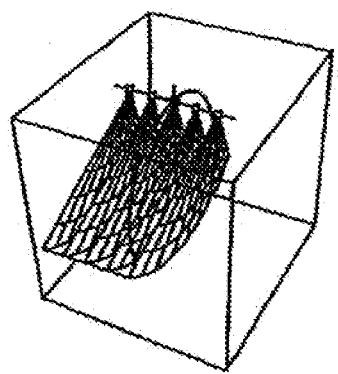
Figure 17:
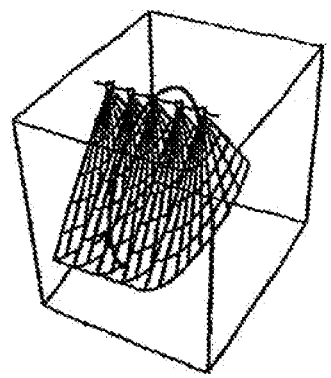
Figure 18:
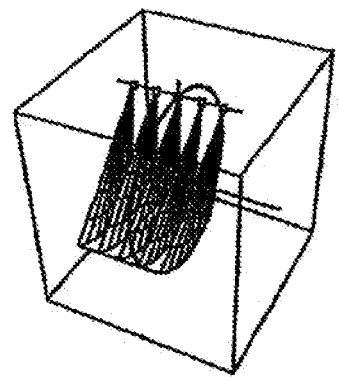
Figure 19:
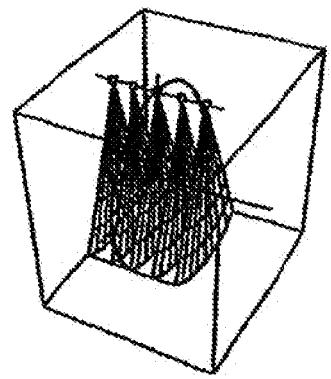

In equations (18) and (19), $\Delta z$ corresponds to the distance between two successive projections on the trajectory line. FIGS. 16 to 19 each exemplify two parallel projections, for the focus detector and for the center detector, respectively. Particularly, FIG. 16 and FIG. 17 show parallel rays parameterized by focus detector coordinates. FIG. 18, FIG. 19 show parallel rays parameterized by center detector coordinates.

Since $v_C$ is fixed for a given parallel projection, equation (15) can be used in order to determine the detector column and the detector row onto which a given object point $x=(x, y, z)$ is projected. For this, $\beta$ and $\sigma$ are first computed, and then these values are used in order to determine $z_0 = z - \sigma v_C$.

In the following, an analysis of the reconstruction scheme, which is preferentially used for reconstruction a final image of the field of interest by using circular first detection data and virtual linear detection data, will be illustrated.

For every position y on the trajectory, the measured projection data $D_f$ can be described by equation (20), which corresponds to the equation (1):

$$D_f(y, \Theta) = \int_0^\infty dl f(y + l\Theta). \quad (20)$$

In other words, line integrals along rays from every position y are considered, pointing in a certain set of directions described by different unit vectors $\theta$. For convenience, $y_l(s) = y_L(z=hs)$ is preferably set for the z-line, where $h>0$ is an arbitrary constant.

A first reconstruction step consists of differentiating the data as follows:

$$D'_f(y(s), \Theta) = \frac{\partial D_f(y(s), \Theta = const.)}{\partial s}. \quad (21)$$

This equation corresponds to the above-mentioned equation (2). Equation (21) means that data are taken from different projections associated with parallel rays which are to be considered. The differentiation step of equation (21) may, for example, be performed with a Fourier filter. Next, the data are filtered with a $1/\sin \gamma$ filter. For this, the filter directions are determined first. They depend on the position of the focal spot and on the point onto which the object point to be reconstructed is projected. Denoting the position of the object point as x, equation (22), which corresponds to equation (5), defines the unit vector b:

$$b(s, x) = \frac{x - y(s)}{|x - y(s)|}. \quad (22)$$

That is to say, b points from the source to the object point. The filter directions can be characterized by means of unit vectors e, which are perpendicular to b. The relationship between e-vectors and filter lines is described in the appendix of "A quasiexact reconstruction algorithm for helical CT using a 3-Pi acquisition" by C. Bontus et al, Med. Phys. 30, 2493-2502 (2003). For every s and for every x, there can be one or more filter directions which have to be used. Using b and e, the filtering step can be described by equation (23), which corresponds to the above-mentioned equation (6):

$$P(s, b) = \sum_{q=1}^{N_f} \int_{-\pi}^{\pi} \frac{d\gamma}{\sin\gamma} D'_f(y(s), \cos\gamma b + \sin\gamma e_q). \quad (23)$$

The summation over q in equation (23) is performed because there can be more than one filter direction. A definition of the vectors e is crucial for the described embodiment. Once the filtered data have been obtained, the back-projection can be written according to equation (24):

$$f(x) = \frac{(-1)}{2\pi^2} \int_I \frac{ds}{|x - y(s)|} P(s, b(s, x)). \quad (24)$$

Within equation (24), "I" denotes the back-projection interval for the respective object point x.

Certainly, the described procedure has to be applied separately to the circular part and to the z-line part of the entire trajectory. In particular, y(s) in equations (21), (23) and (24) corresponds to either $y_0(s)$ or $y_l(s)$. Finally, the two results of equation (24) are added together.

If a rebinning into parallel geometry is performed after the filtering step in equation (23), the back-projection formula of equation (24) changes. In particular, the formula for the circular part is the same as given in WO 2004/044849 A1. For the z-line part, the back-projection has to be formed via equation (25):

$$f(x) = \frac{(-1)}{2\pi^2} \frac{1}{h} \int dv_f \frac{\cos\lambda}{R} P(v_F, b(v_F, x)), \quad (25)$$

if the parallel data are parameterized by focus detector coordinates, and via $$f(x) = \frac{(-1)}{2\pi^2} \frac{1}{h} \int dv_C \frac{\cos\lambda}{l} P(v_C, b(v_C, x)), \ l = 2R\cos\beta, \quad (26)$$

if the parallel data are parameterized by center detector coordinates. In these equations, h was introduced above in defining $y_l(s) = Y_L(z=hs)$, and $\lambda$ corresponds to the cone angle of a particular ray. The value of $\lambda$ can be computed from equation (27):

$$\tan\lambda = \frac{v_F}{D} = \frac{v_C}{l} \quad (27)$$

An advantage of equations (25) and (26) compared with equation (24) is that no object-point dependent factor |x-y| needs to be computed. This significantly reduces the calculation time by reducing the computational burden for calculating a reconstructed image. The filtered data have to be multiplied only by factors that depend on the detector coordinates $\alpha$, $\beta$, $v_F$ or $v_C$.

In the following, an analysis of filter lines for the circular part will be described.

As described in the cited "A quasiexact reconstruction algorithm for helical CT using a 3-Pi acquisition" by C. Bontus et al, Med-Phys. 30, 2493-2502 (2003), it may be advantageous to introduce a virtual planar detector containing the rotation axis. Coordinates on this detector are denoted $u_{PL}$ and $v_{PL}$, and the $v_{PL}$-axis is parallel to the z axis. A line is considered containing the source and perpendicular to the planar detector. The point ($u_{PL}$=0, $v_{PL}$=0) corresponds to the point in which this line intersects the planar detector. Now, each filter line can be described according to equation (28):

$$v_{Pl}(u_{Pl}) = v_0 + \sigma u_{Pl} \quad (28)$$

In other words, it corresponds to a straight line on the planar detector. In general, the gradient σ is different for different filter lines.

For the described algorithm, the data obtained are filtered on the circular part along lines parallel to the $u_{PL}$-axis, that is to say $v_{PL}(U_{PL})=v_0$. The different lines are parameterized by $v_0$. The filter direction goes from left to right.

In the following, an analysis of the filter lines for the z line part, i.e. the virtual detection data, will be described.

For the parameterization of the filter lines for the z-line part, first the projection of the circle onto the planar detector as seen from a source at z=$z_0$ will be considered. In particular, this projection can be described as $$v_{Pl}(u_{Pl}) = -\frac{z_0}{2}\left[1 + \left(\frac{u_{Pl}}{R}\right)^2\right]. \quad (29)$$

FIG. 20 and FIG. 21 show the projections of the circle for two different $z_0$. Particularly, FIG. 20 shows a projection of the circle onto the planar detector seen from $z_0$<0. FIG. 21 shows a projection of the circle onto the planar detector seen from $z_0$>0. The detector area is divided into two regions A and B as shown in FIG. 20 and FIG. 21. If the object-point is projected into region A, the projection data associated with a current source position is not used for the reconstruction. Therefore, the data in region A should be set to zero. For region B, preferred filter lines are defined in the following.

A line tangential to the projected circle can be parameterized using equation (30):

$$v_{Pl}(u_{Pl}) = -\frac{z_0}{2}\left[1 + \left(\frac{u_0}{R}\right)^2\right] - \frac{z_0 u_0}{R^2}(u_{Pl} - u_0). \quad (30)$$

In equation (30), $u_0$ is the coordinate at which the line is tangential. In particular, if one looks for the tangential line containing the point ($u_1$, $v_1$), the parameter $u_0$ can be computed according to equation (31):

$$u_0 = u_1 \pm \sqrt{u_1^2 + R^2\left(1 + 2\frac{v_1}{z_0}\right)}. \quad (31)$$

The sign in front of the square root has to be chosen in dependence on whether the tangential point is desired to be located left (minus) or right (plus) of ($u_1$, $v_1$).

The filter lines are sets of lines which are tangential to the projected circle. FIGS. 22 to 25 exemplify these lines. FIG. 22, FIG. 23 show filter lines with different filter directions from left to right. FIG. 24, FIG. 25 show filter lines with filter directions from right to left. In particular, the contributions of different filter lines are used for each point ($u_{PL}$, $v_{PL}$). Details on how these filter lines should be used for the combination of a circle and line acquisition are disclosed in "Image reconstruction for the circle and line trajectory" by A. Katsevich, Phys. Med. Biol., 49, 5059-5072 (2004).

The reconstructed image of the field of interest is shown on the display unit 11 and the method of imaging a field of interest ends in step 106.

In the embodiment described above, short-scan data are used which correspond to exactly 180° on the first trajectory, which in this embodiment is a circular trajectory. In another embodiment over-scan data are also used. In order to use these over-scan data, the reconstruction of an intermediate image in step 103, the forward-projection in step 104, and the final reconstruction in step 105 are repeated for slightly different back-projection intervals along the first trajectory which is, in particular, a circular trajectory. An image of a field of view is reconstructed for each of these slightly different back-projection intervals, and these reconstructed images are averaged with the use of appropriately chosen weights.

For instance, if $s_0$ is the starting angle of the preferred back-projection interval, similar reconstructions can be performed for starting angles $s_0$−5°, −2.5°, $s_0$+2.5°, and $s_0$+5°. The resulting image data may be added up using weights 1/9, 2/9, 3/9, 2/9, 1/9 for the images obtained with starting angles $s_0$−5°, $s_0$−2.5°, $s_0$, $s_0$+2.5°, and +5°, respectively.

Averaging may also be performed during the reconstruction step 105. If, for example, in step 105 the first detection data are back-projected as described above, the first detection data can be weighted with appropriately chosen weights before the first detection data are back-projected, i.e. the first detection data, which have been weighted with these appropriately chosen weights, are back-projected.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure, and the appended claims.

For example, the invention is not limited to a first trajectory being a circular trajectory, a second trajectory being a helical trajectory, and a virtual trajectory being a line parallel to the z-axis. The invention may comprises any trajectory whatsoever. For example, the virtual trajectory may also be a helical trajectory, and the second trajectory may be a line parallel to the z-axis.

The invention may also be used if the field of interest does not contain any moving element. Furthermore, the field of interest may comprise only technical objects.

The invention allows, in particular, a circular short-scan reconstruction resulting in an excellent temporal resolution. Furthermore, in combination with a fast rotating CT scanner, a single-cycle cardiograph reconstruction becomes possible. In particular, the invention renders it possible, furthermore, to acquire data along the second trajectory with a very low dose in an ungated manner, even if moving elements, like the human heart, are present within the field of interest.

In the claims, the word "comprising" does not exclude other elements or steps, and the indefinite article "a" or "an" does not exclude a plurality.

A computer program may be stored/distributed on a suitable medium, such as an optical storage medium or a solid-state medium supplied together with or as part of other hardware, or may alternatively be distributed in other forms, such as via the Internet or other wired or wireless telecommunication systems.

Any reference signs in the claims should not be construed as limiting the scope.

The invention claimed is:

1. An imaging system for imaging a field of interest, comprising:
    an irradiation unit that emitts radiation for irradiating the field of interest,
    a moving unit for that moves the irradiation unit relative to the field of interest along
    a first trajectory and that moves the irradiation unit along a second trajectory,
    a detection unit that detects first detection data depending on the radiation after passing through the field of interest when the irradiation unit is moved along the first trajectory, and that detects second detection data depending on the radiation after passing through the field of interest when the field of interest is irradiated along the second trajectory,
    a reconstruction unit that reconstructs an intermediate image of the field of interest from at least the second detection data and that reconstructs an image of the field of interest from the first detection data which correspond to one or several sections on the first trajectory, and virtual detection data,
    a forward-projection unit that determines the virtual detection data by forward projection through the intermediate image,
    wherein the first trajectory is arranged within a plane that intersects the field of interest and wherein the second trajectory is arranged at least partially outside said plane,
    wherein the forward-projection unit is adapted such that the forward projection is done along a virtual trajectory arranged such that it matches the first detection data which are used to reconstruct the image of the field of interest, so as to obtain complete data for reconstructing the image of the field of interest,
    wherein the forward-projection unit is adapted such that the virtual trajectory is arranged such that it intersects the plane at the one or several sections on the first trajectory.

2. The imaging system as claimed in claim 1,
    wherein the moving unit is adapted such that the first trajectory is a circular trajectory.

3. The imaging system as claimed in claim 1,
    wherein the moving unit is adapted such that the second trajectory is a helical trajectory.

4. The imaging system as claimed in claim 3, wherein the helical trajectory has a non-zero pitch.

5. The imaging system as claimed in claim 1,
    wherein the forward-projection unit is adapted such that the virtual trajectory is arranged such that it intersects the plane at an endpoint of the one or several sections on the first trajectory.

6. The imaging system as claimed in claim 1,
    wherein the forward-projection unit is adapted such that the virtual trajectory is a line perpendicular to the plane.

7. The imaging system as claimed in claim 1,
    wherein the reconstruction unit is adapted such that the first detection data, which are used to reconstruct the image of the field of interest, are short-scan data.

8. The imaging system as claimed in claim 1,
    wherein the reconstruction unit is adapted such that the first detection data, which are used to reconstruct the image of the field of interest, comprise several short-scan data sets, wherein different short-scan data sets correspond to different sections on the first trajectory.

9. The imaging system as claimed in claim 1,
    wherein the reconstruction unit is adapted such that reconstructing the intermediate image comprises the following steps:
    reconstructing voxels of the intermediate image which have not been irradiated over an angular range of 360° along the first trajectory, by using the second detection data,
    reconstructing voxels of the intermediate image which have been irradiated over an angular range of 360° along the first trajectory, by using the first detection data and the second detection data.

10. The imaging system as claimed in claim 1, wherein the reconstruction unit is adapted for exactly reconstructing at least one of the intermediate image and the image of the field of interest, which is reconstructed from the first detection data and the virtual detection data.

11. The imaging system as claimed in claim 1, wherein the first trajectory and the second trajectory are different trajectories.

12. The imaging system as claimed in claim 1, wherein neither the first trajectory nor the second trajectory is a virtual trajectory.

13. The imaging system as claimed in claim 1, wherein the first detection data is not derived from the second detection data and the second detection data is not derived from the first detection data.

14. An image generation device for generating an image of a field of interest, the image generation device being provided with first detection data detected by a detection unit when an irradiation unit emitting radiation for irradiating the field of interest is moved relative to the field of interest along a first trajectory, the first detection data being dependent on the radiation after passing through the field of interest, and the image generation device being provided with second detection data detected by the detection unit when the irradiation unit is moved relative to the field of interest along a second trajectory, the second detection data being dependent on the radiation after passing through the field of interest, the first trajectory being arranged within a plane that intersects the field of interest and the second trajectory being arranged at least partially outside said plane, comprising:
    a reconstruction unit for reconstructing an intermediate image of the field of interest from at least the second detection data and for reconstructing an image of the field of interest from the first detection data, which correspond to one or several selections on the first trajectory, and virtual detection data,
    a forward-projection unit for determining the virtual detection data by forward projection through the intermediate image,
    wherein the forward-projection unit is adapted such that the forward projection is done along a virtual trajectory arranged such that it matches the first detection data which are used to reconstruct the image of the field of interest, so as to obtain complete data for reconstructing the image of the field of interest,
    wherein the forward-projection unit is adapted such that the virtual trajectory is arranged such that it intersects the plane at the one or several sections on the first trajectory.

15. An imaging method for imaging a field of interest, comprising the steps of:
    irradiating the field of interest by means of an irradiation unit that emits radiation, moving the irradiation unit relative to the field of interest along a first trajectory and along a second trajectory by means of a moving unit, wherein the first trajectory is arranged within a plane that intersects the field of interest and wherein the second trajectory is arranged at least partially outside said plane, detecting first detection data depending on the radiation after passing through the field of interest, when the irradiation unit is moved along the first trajectory, and detecting second detection data depending on the radiation after passing through the field of interest, when the field of interest is irradiated along the second trajectory, by means of a detection unit, reconstructing an intermediate image of the field of interest from at least the second detection data by means of a reconstruction unit, determining virtual detection data by forward projection through the intermediate image by means of a forward-projection unit, wherein the forward projection is done along a virtual trajectory arranged such that it matches first detection data which are used to reconstruct the image of the field of interest, so as to obtain complete data for reconstructing the image of the field of interest, and wherein the virtual trajectory is arranged such that it intersects the plane at one or several sections on the first trajectory, reconstructing an image of the field of interest from the first detection data, which correspond to the one or several sections on the first trajectory, and the virtual detection data by means of the reconstruction unit.

16. A computer program for imaging a field of interest, comprising program code means for causing an imaging system to carry out the steps of the method as claimed in claim 15 when the computer program is run on a computer.

17. The imaging method as claimed in claim 15, wherein the first trajectory and the second trajectory are different trajectories.

18. The imaging method as claimed in claim 15, wherein neither the first trajectory nor the second trajectory is a virtual trajectory.

19. An image generation method for generating an image of a field of interest, the image generation method using first detection data detected by a detection unit when an irradiation unit emitting radiation for irradiating the field of interest is moved relative to the field of interest along a first trajectory, the first detection data being dependent on the radiation after passing through the field of interest, and the image generation method using second detection data detected by the detection unit when the irradiation unit is moved relative to the field of interest along a second trajectory, the second detection data being dependent on the radiation after passing through the field of interest, the first trajectory being arranged within a plane that intersects the field of interest and the second trajectory being arranged at least partially outside said plane, comprising the steps of:

reconstructing an intermediate image of the field of interest from at least the second detection data by means of a reconstruction unit, determining virtual detection data by forward projection through the intermediate image by means of a forward-projection unit, wherein the forward projection is done along a virtual trajectory arranged such that it matches first detection data which are used to reconstruct the image of the field of interest, so as to obtain complete data for reconstructing the image of the field of interest, and wherein the virtual trajectory is arranged such that it intersects the plane at one or several sections on the first trajectory, reconstructing an image of the field of interest from the first detection data, which correspond to the one or several sections on the first trajectory, and the virtual detection data by means of the reconstruction unit.

20. A computer program for generating an image of a field of interest, comprising program code means for causing a computer to carry out the steps of the method as claimed in claim 19 when the computer program is run on a computer.

* * * * *